United States Patent [19]
Critchley

[11] Patent Number: 5,658,905
[45] Date of Patent: Aug. 19, 1997

[54] USE OF TRIAZINE COMPOUNDS AS ANXIOLYTICS

[75] Inventor: Martyn Alan Edwin Critchley, Beckenham, Great Britain

[73] Assignee: Glaxo Wellcome Inc., Research Triangle Park, N.C.

[21] Appl. No.: 535,139

[22] PCT Filed: Mar. 18, 1994

[86] PCT No.: PCT/GB94/00560

§ 371 Date: Sep. 18, 1995

§ 102(e) Date: Sep. 18, 1995

[87] PCT Pub. No.: WO94/21261

PCT Pub. Date: Sep. 29, 1994

[30] Foreign Application Priority Data

Mar. 19, 1993 [GB] United Kingdom ............... 9305692

[51] Int. Cl.⁶ ..................................... A61K 31/53
[52] U.S. Cl. ................................................ 514/242
[58] Field of Search ................................... 514/242

[56] References Cited

FOREIGN PATENT DOCUMENTS

| 0 021 121 | 1/1981 | European Pat. Off. . |
| 0 517 347 | 12/1992 | European Pat. Off. . |

OTHER PUBLICATIONS

British J. Pharmacol. III, Suppl. 205P (1994).
Epilepsia 32 (Suppl. 2) SA–S8 (1991).
Can. J. Neurol. Sci. 19 1 (Suppl.) (1992) 160–162.
Boll. Lega Ital. Epilespssia 70/71 (1990), 103–104.

*Primary Examiner*—Phyllis G. Spivack
*Attorney, Agent, or Firm*—Nixon & Vanderhye P.C.

[57] ABSTRACT

A method of treating anxiety is disclosed comprising administering 3,5-diamino-6-(2,3-dichlorophenyl)-1,2,4-triazine or a pharmaceutically acceptable acid addition salt thereof.

9 Claims, 1 Drawing Sheet

USE OF TRIAZINE COMPOUNDS AS ANXIOLYTICS

This application is a 371 of PCT/GB 94/00560 filed Mar. 18, 1994.

The present invention relates to the use of 3,5-diamino-6-(2,3-dichlorophenyl)-1,2,4-triazine and its pharmaceutically and veterinarily acceptable acid addition salts in therapy.

EP-A-0 021 121 describes a group of triazines, including 3,5-diamino-6-(2,3-dichlorophenyl)-1,2,4-triazine, which are active in the treatment of disorders of the central nervous system, for example psychiatric and neurological disorders, and which are particularly useful as anticonvulsants for instance in the treatment of epilepsy. These triazines are non-depressant and are therefore advantageous compared with depressant anti-epileptics such as phenobarbitone. EP-A-0 247 892 describes 3,5-diamino-6-(2,3-dichlorophenyl)-1,2,4-triazine isethionate, a particularly preferred salt owing to its good solubility.

In mechanistic studies, 3,5-diamino-6-(2,3-dichlorophenyl)-1,2,4-triazine has been shown to produce a use-dependent block of voltage-sensitive sodium channels (Lang et at, 1993, J. Pharm. Exp. Therap., 266, 829; Lees, G. and Leach, M. J., 1993, Brain Res., 612, 190) and at anticonvulsant brain concentrations to inhibit the release of excitatory. amino acids, principally glutamate (Leach, M. J. et at, 1986, Epilepsia, 27, 490–497; Zhu, S. G. and McGee, E. G., 1990, Neurosci. Lett., 112, 348–351). Glutamate functions as an important neurotransmitter in the mammalian central nervous system and has also been identified as having specific actions in the peripheral nervous system. The known anticonvulsant effect of this compound has therefore been ascribed to its ability to act at voltage-sensitive sodium channels as an inhibitor of glutamate release.

Anxiety is a symptom associated with a wide range of clinical conditions. Conventional anxiety management includes treatment with sedative anxiolytics, examples of which are benzodiazepines such as diazepam (7-chloro-1,3-dihydro-1-methyl-5-phenyl-2H-1,4-benzodiazepin-2-one). However, the clinical use of benzodiazepines is associated with adverse side-effects including dependence and ataxia. There is therefore a continuing need for new agents which are effective anxiolytics.

It has now surprisingly been found that 3,5-diamino-6-(2,3-dichlorophenyl)-1,2,4-triazine and its salts are effective in controlling anxiety. Accordingly, the present invention provides the use in the preparation of a medicament for the treatment of anxiety or an anxiety disorder, of 3,5-diamino-6-(2,3-dichlorophenyt)-1,2,4-triazine or a pharmaceutically or veterinarily acceptable acid addition salt thereof.

3,5-Diamino-6-(2,3-dichlorophenyl)-1,2,4-triazine will hereinafter be referred to as compound A. Compound A and its salts will be referred to collectively as the present compounds. The present compounds are non-toxic at prophylactically and therapeutically effective doses. They have the important added advantage over benzodiazepines such as diazepam that their use does not give rise to dependence or to behavioural changes such as ataxia (see Example 1 and the Comparative Example which follow).

Suitable acid addition salts of compound A include those formed with both organic and inorganic acids. Such acid addition salts will normally be pharmaceutically and veterinarily acceptable. Examples of such salts include those formed with hydrochloric, sulphuric, citric, tartaric, phosphoric, lactic, pyruvic, acetic, succinic, fumaric, maleic, methanesulphonic, ethanesulphonic, oxaloacetic and isethionic acids. The salt with isethionic acid is preferred since it possesses particularly good solubility.

The present compounds may be prepared by a process which comprises cyclising the compound of formula (II):

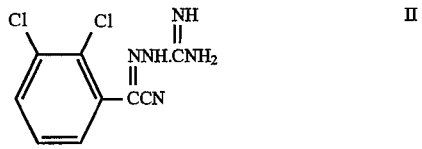

and, if desired, converting compound A thus obtained into a pharmaceutically or veterinarily acceptable acid addition salt.

The cyclisation is typically carried out by heating the compound of formula II under reflux in an alkanol, preferably a $C_{1-4}$ alkanol, for example methanol or ethanol, in the presence of a strong base, for example potassium hydroxide. The process may, for instance, be carried out as described in Example 1 of EP-A-0 021 121. The optional subsequent step of converting the compound A into an acid addition salt is performed by a conventional method, for example by treatment with the appropriate acid at ambient temperature. The salt with isethionic acid may be prepared, for instance, as described in EP-A-0 247 892, in particular in Example 3.

The starting compound of formula II may be prepared by the method described in U.S. Pat. No. 3,637,688.

Anxiety disorders are defined, in the Diagnostic and Statistical Manual of Mental Disorders (Third Edition - Revised, 1987, published by the American Psychiatric Association, Washington, D.C., U.S.A., see pages 235 to 253), as psychiatric conditions having symptoms of anxiety and avoidance behaviour as characteristic features.

Generalised anxiety disorder is a condition of which the essential feature is unrealistic or excessive anxiety and worry about two or more life circumstances for six months or longer. During that time the affected person is bothered by the concerns for more days than not. When the person is anxious he or she manifests signs of motor tension, autonomic hyperactivity and vigilance and scanning.

Simple phobia is an anxiety disorder of which the essential feature is a persistent fear of a circumscribed stimulus, which may be an object or situation, other than fear of having a panic attack (as in panic disorder, referred to below) or of humiliation or embarrassment in social situations (which falls under social phobia). Simple phobias may be referred to as "specific" phobias and, in the population at large, most commonly involve animals such as dogs, snakes, insects and mice. Other simple phobias involve witnessing blood or tissue injury. (blood-injury phobia), closed spaces (claustrophobia), heights (acrophobia) or air travel. Exposure to the phobic stimulus will almost invariably lead to an immediate anxiety response.

Panic disorder is a condition characterised by recurrent panic attacks, i.e. discrete periods of intense fear or discomfort with at least four characteristic associated symptoms. The attacks usually last minutes (or, rarely, hours), are unexpected and do not, as in simple phobia, tend to occur immediately before or on exposure to a situation that almost always causes anxiety. The "unexpected" aspect of the attacks is an essential feature of the disorder. Panic attacks typically begin with the sudden onset of intense apprehension or fear, and are accompanied by physical symptoms such as shortness of breath, dizziness, faintness, choking, palpitations, trembling, sweating, shaking, nausea, numbness, hot flushes or chills, chest pain and so on. Panic disorder may be associated with agoraphobia, in severe cases of which the person concerned is virtually housebound.

Besides being central to anxiety disorders as such, anxiety occurs as a symptom associated with other psychiatric disorders and also with organic clinical conditions.

In obsessive compulsive disorder (OCD, also called obsessive compulsive neurosis), for instance, the primary symptom is recurrent obsessions or compulsions of sufficient severity to cause distress, be time consuming or to interfere significantly with a person's normal routine or lifestyle. Anxiety is an associated feature of this disorder: an affected person may, for example, show a phobic avoidance of situations that involve the cause of the obsession.

A further example of such psychiatric disorders is post-traumatic stress disorder. The principal characteristic symptoms of this involve re-experiencing a traumatic (i.e. psychologically distressing) event, the avoidance of stimuli associated with that event, the numbing of general responsiveness, and increased arousal. The "events" concerned are outside the range of common experiences such as simple bereavement, chronic illness and marital conflict; examples include a serious threat to one's life or the life of one's children spouse or other close relative and the witnessing of another person's death or injury in an accident or following physical violence. Anxiety is a symptom commonly associated with this condition.

Other psychiatric conditions of which anxiety is an associated symptom include schizophrenia, mood disorders and major depressive disorders.

Finally, organic clinical conditions with which anxiety symptoms may be associated include Parkinson's disease, multiple sclerosis and other physically incapacitating disorders.

An animal model of anxiety which is suitable for testing potential anxiolylic agents is the Vogel conflict (punished drinking) model in rats (Vogel, J. R. et al, 1971. Psychopharmacol., 21, 1–7). As in other animal models based on a conflict procedure, in the Vogel conflict model the suppression by punishment of the animal's desire to respond results in a state of conflict which can be likened to the human state of anxiety.

Administration of drugs with anxiolytic properties will release the punishment-suppressed responding. In this particular model this is manifested as an increase in the number of licks (attempts to drink) during punishment when compared with a vehicle control.

The Vogel conflict test gained widespread use over the past 20 years or so and has proved to be a selective screening test for anti-anxiety drugs, with a good correlation with clinically effective anxiolytics. Furthermore, the testing of a range of psychoactive non-anxiolytic drugs has failed to produce false positives in the test (Vogel J. R. et al, ibid; Cook L. and Sepinwall, J., 1975: Behavioural analysis of the effects and mechanisms of action of benzodiazepines, in "Mechanisms of Action of Benzodiazepines", ed. Costa. E. and Greengard. P., New York Raven Press. pages 1 to 28: McCowen, T. J. et al 1983. Pharmacol. Biochem. Behav., 18, 277–279).

The present compounds are active in the Vogel conflict model, as demonstrated in Example 1 which follows. The present compounds are therefore anxiolytics. Accordingly, the present invention provides a method of treating anxiety or an anxiety, disorder in a mammal, the method comprising administering thereto a therapeutically effective amount of one of the present compounds. In this way anxiety can be controlled and/or alleviated. The condition of a human being or animal can thereby be improved.

The present compounds have utility in treating anxiety disorders, as defined above, and also anxiety which occurs as a symptom associated with clinical conditions of either psychiatric or organic origin. Examples of anxiety disorders which the present compounds may be used to treat therefore include generalised anxiety disorder, simple phobia and panic disorder. The present compounds are also useful in treating anxiety which is associated with psychiatric conditions such as obsessive compulsive disorder, post-traumatic stress disorder, schizophrenia, mood disorders and major depressive disorders, and with organic clinical conditions such as Parkinson's disease and multiple sclerosis.

The present compounds are non-toxic at prophylactically and therapeutically effective doses. The orientative acute oral toxicity ($LD_{50}$) for compound A in mice is 250 mg/kg and in rats is 640 mg/kg. These are the dose levels at which 50% of the animals survive 10 days after administration of compound A.

The present compounds can be administered by a variety of routes and in a variety of dosage forms including those for oral, rectal, parenteral (such as subcutaneous, intramuscular and intravenous), epidural, intrathecal, intra-articular, topical and buccal administration.

The present compounds may be administered in any of the above dosage forms at a dose of from 1 mg/kg to 40 mg/kg per day, for example 5 mg/kg to 40 mg/kg, suitably 10 mg/kg to 30 mg/kg. For oral administration a dose of 40 mg/kg is particularly suitable. The dose range for adult human beings will depend on a number of factors including the age, weight and condition of the patient and the administration route. A typical dosage regimen is from 20 mg to 3200 mg per day, typically from 350 mg to 1400 mg per day, preferably from 600 mg to 1070 mg per day. It may in some situations be advantageous, since the present compounds are long-acting, to administer an initial dose of 70 mg to 3200 mg on the first day of treatment and then a lower dose of 20 mg to 1600 mg on subsequent days (all doses expressed as the base).

The present invention further provides a composition comprising a pharmaceutically or veterinarily acceptable carrier or diluent and, as an active principle, one of the present compounds. The composition can be prepared using conventional methods and administered in a pharmaceutically acceptable form.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening or emulsifying agents can be included. When a suspension is prepared in water according to the present invention at least one of such agents will be present.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols: gelling agents such as colloidal clays: thickening agents such as gum tragacanth or sodium alginate: binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures: dyestuffs; sweeteners: wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which metabolise only a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injection may contain, together with the active compound, a pharmaceutically acceptable carrier such as sterile water, olive oil, ethyl oleate, glycols such as propylene glycol and, if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compounds may be encapsulated within liposomes.

The present compounds may also be administered in pure form unassociated with other additives, in which case a capsule, sachet or tablet is the preferred dosage form.

Tablets and other forms of presentation provided in discrete units conveniently contain a daily dose, or an appropriate fraction thereof of one of the present compounds. For example units may contain from 5 mg to 500 mg, but more usually from 10 mg to 250 mg, of one of the present compounds (expressed as the base).

The invention is further illustrated in the Examples which follow.

EXAMPLE 1

Figure 1:
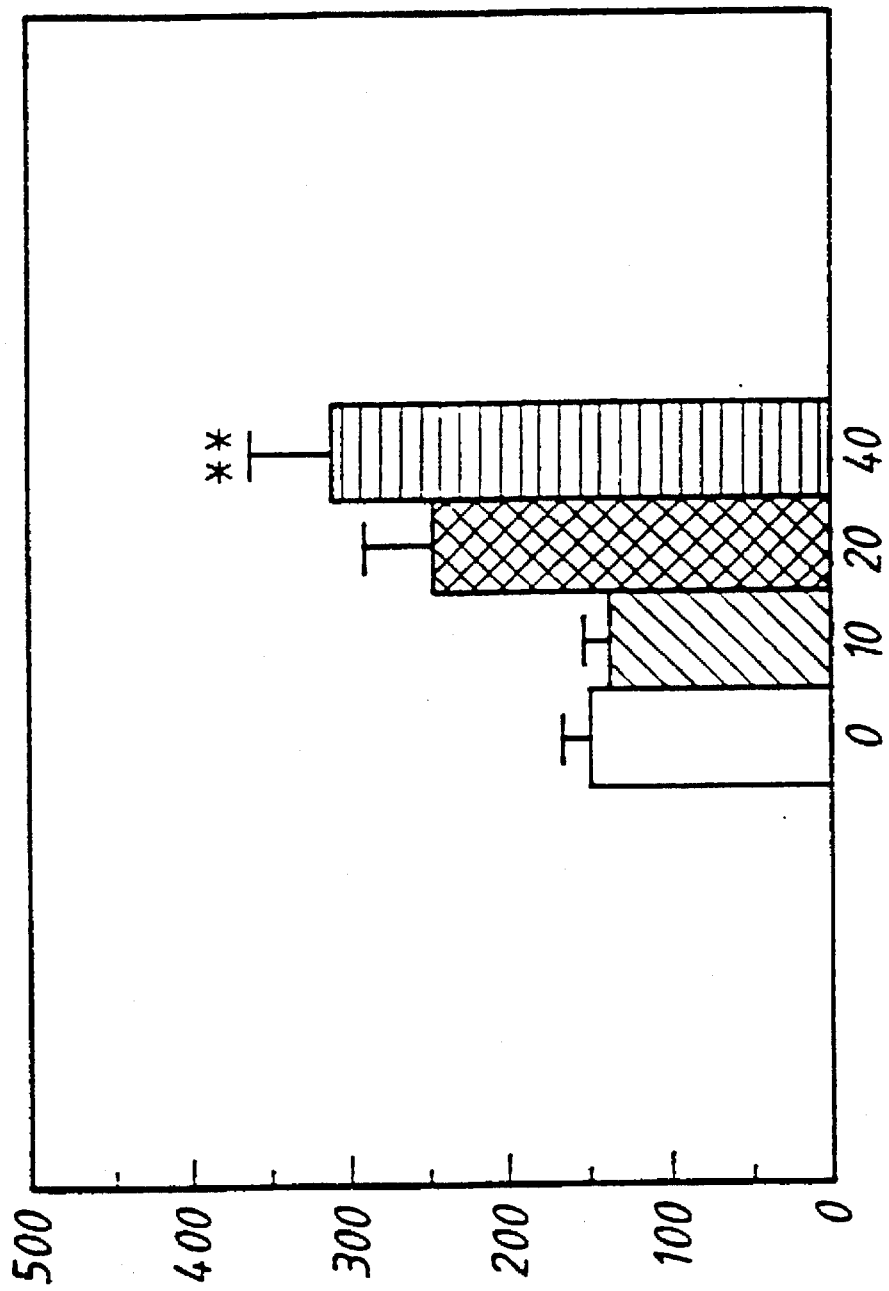
FIG. 1 is a graph of mean number of licks (±s.e.m., y axis) per 5-minute session for compound A isethionate at doses of 0, 10, 20 and 40 mg/kg base equivalent in the rat model test of Example 1.

Testing of compound A in the Vogel conflict model of anxiety in rats
Methods & Materials
Animals Male hooded Lister rats (Charles River), 150–200 g, were maintained in groups of 7–10 and given food ad libitum. 24-Hours prior to the test the water bottles were removed from the home cages.
Apparatus The apparatus consisted of an operant conditioning chamber (Skinner box) which contained a grid floor and an externally mounted drinking bottle, the spout of which was accessible from inside the chamber. The chamber was housed inside a ventilated sound-attenuating box. Licks at the spout were detected by "Drinkometer" circuitry, (Campden Instruments Ltd., London W8 7TH, U.K.) whereby contact between the grid floor and drinking spout completed a circuit. Experimental control was performed by a "Spider" microcomputer system (Paul Fray Ltd., Waterbeach, Cambridge CB5 9QZ, U.K.) which counted licks from the "Drinkometer" circuit, controlled session timers and shock delivery from a constant current shock generator (Campden Instruments Ltd.) and produced raw data printouts.
Procedure On the morning of the test day (18–20 hours water deprivation) the animals were individually placed in the chamber and allowed a 5-minute shock-free session in which to familiarise themselves with the drinking spout and initiate licking (pre-test). Accumulation of 500 licks terminated the session. Rats not achieving the required 500 licks within the 5 minutes were not used. After a further period of water deprivation (up to the total of 24 hours) and the required drug/vehicle pretreatments, the rats were individually replaced in the chamber. For this second part of the test the animals were allowed 40 licks at the spout before a 5-minute session was automatically triggered by the 41st lick. During this 5-minute session, every 20th lick at the spout was accompanied by a small electric shock (0.075 mA for 0.5 seconds) delivered between the spout and the grid floor. The shock was always avoidable, being contingent on licks from the drinking bottle, and was terminated when contact with the spout was broken. The number of licks was recorded.
Statistics Statistical comparisons were made using a Mann-Whitney U-test. This non-parametric test was appropriate since it is not always acceptable to make assumptions concerning the population in these types of behavioural experiments. p Values of less than 0.05 were regarded as indicating significant effects. Since the Mann-Whitney test ranks the raw data it relies on ordinal scaling. In such cases it is not strictly valid to express the results as a mean ±standard error. However, for the purposes of clarity in expressing the results, means and standard errors have been used.
Compounds used The isethionate salt of compound A was dissolved in distilled water and administered orally, in a volume of 5 ml/kg, one hour before test. Control animals received water vehicle alone.

The results (number of licks) are shown in the following Table 1 and in the accompanying FIG. 1.

TABLE 1

| | Dose p.o. (mg/kg base equivalent) | | |
|---|---|---|---|
| | 10 | 20 | 40 |
| Compound A isethionate | 92 | 165 | 208 |

The data are expressed as percentage of vehicle control responding [vehicle=100%]. Increases above 100% represent anxiolytic effects and decreases represent anxiogenic effects. The highlighted figure represents a statistically significant ($p<0.05$) anxiolytic effect.

FIG. 1 shows that compound A isethionate produced a dose-related increase in punished responding at 20 and 40 mg/kg, that at the latter dose being significant. Importantly, no other behavioural changes were observed.

COMPARATIVE EXAMPLE

Testing of reference compounds in the Vogel conflict model of anxiety in rats

Using the methods and materials described in Example 1, the following compounds were tested: diazepam (10 mg ampoules, Roche), known anxiolytic, used as positive control, and the standard anticonvulsants carbamazepine (Sigmna) and phenytoin* (Sigma). The diazepam was diluted from the ampoules using distilled water and administered subcutaneously (2 ml/kg) 20 minutes before test. Carbamazepine and phenytoin were suspended in 0.25% (w/v) aqueous celacol using a ballmill and administered orally at 5 ml/kg, one hour before test.
* sodium salt; doses expressed as parent acid equivalent The results (number of licks) are shown in the following Table 2.

TABLE 2

| Compound | Dose (mg/kg) | | | | | |
|---|---|---|---|---|---|---|
| | 0.5 | 1.0 | 5.0 | 10.0 | 20.0 | 40.0 |
| Diazepam (s.c.) | __162__ | __296__ | | | | |
| Carbamazepine (p.o.) | | | 87 | | 161 | |
| Phenytoin (p.o.) | | | | | 121 | 114 |

The data are expressed as percentage of vehicle control responding [vehicle=100%]. Increases above 100% represent anxiolytic effects and decreases represent anxiogenic effects. The highlighted figures represent statistically significant (p<0.05) anxiolytic effects.

The results show that diazepam produced a dose-related increase in punished responding (PR) at 0.5 and 1.0 mg/kg. This effect was large and significant. However, at 1.0 mg/kg it was accompanied by ataxia, a result of the muscle relaxant effect which commonly occurs with benzodiazepines.

Carbamazepine and phenytoin were tested as they have anticonvulsant properties in common with compound A and its salts. However, carbamazepine produced no effect at 5.0 mg/kg and a non-significant increase in PR at 20 mg/kg. Phenytoin produced no effect on PR at either 10 or 40 mg/kg.

In a further series of tests, again using the methods and materials described in Example 1, the following compounds were evaluated:

| standard anticonvulsants: | carbamazepine |
| | ethosuximide |
| | phenytoin sodium |
| | sodium valproate |
| 5-HT$_3$ receptor antagonists: | bemesetron (MDL 72222) |
| | ondansetron hydrochloride |

Bemesetron was administered in a mixture of dimethyl sulphoxide and distilled water, the rest in 0.25% (w/v) aqueous celacol; all were given one hour before test at 5 ml/kg.

The results (number of licks) are shown in the following Table 3; for salts, doses are expressed as equivalent of the parent moiety.

TABLE 3

| Compound | Dose p.o. (mg/kg)* | | | | | | | | | |
|---|---|---|---|---|---|---|---|---|---|---|
| | 0.1 | 0.5 | 1.0 | 10 | 20 | 40 | 80 | 100 | 160 | 320 |
| Carbamazepine | | | | __154__ | __206__ | __219__ | __309__ | | | |
| Ethosuximide | | | | | | 64 | 133 | | 61 | 96 |
| Phenytoin sodium | | | | | 101 | 135 | 220 | | 173 | |
| Sodium valproate | | | | | | 79 | 108 | | 151 | 261 |
| Bemesetron | 89 | 129 | 156 | | | | | 116 | | |
| Ondansetron hydrochloride | 68 | 80 | 70 | | | | | 87 | | |

*Bemesetron and ondansetron hydrochloride doses in µg/kg

The data are expressed as percentage of vehicle control responding [vehicle=100%]. Increases above 100% represent anxiolytic effects and decreases represent anxiogenic effects. The highlighted figures represent statistically significant (p<0.05) anxiolytic effects.

The results show that only carbamazepine produced a dose-related, significant increase in punished responding.

The 5-HT$_3$ receptor antagonists, bemesetron and ondansetron, have been reported to exhibit anxiolytic effects in other animal models. Their lack of any significant anxiolytic effect in the Vogel conflict model, in contrast with compound A isethionate (Example 1), suggests that this property of compound A and its salts is not mediated via the 5-HT$_3$receptor.

EXAMPLE 2

Pharmaceutical composition

Tablets for oral administration are formulated with the following ingredients:

| | |
|---|---|
| Compound A | 150 mg |
| Lactose | 200 mg |
| Maize starch | 50 mg |
| Polyvinylpyrrolidone | 4 mg |
| Magnesium stearate | 4 mg |

Mix the active compound with the lactose and starch and granulate with a solution of the polyvinylpyrrolidone in water. Dry the resulting granules, mix with the magnesium stearate and compress to give tablets of average weight 408 mg.

I claim:

1. A method of treating anxiety or an anxiety disorder in a mammal, the method comprising administering thereto a therapeutically effective amount of a compound selected from 3,5-diamino-6-(2,3-dichlorophenyl)-1,2,4-triazine and a pharmaceutically veterinarily acceptable acid addition salt thereof.

2. The method according to claim 1 wherein the mammal is man.

3. A method according to claim 1 where the acid addition salt is 3,5-diamino-6-(2,3-dichlorophenyl)-1,2,4-triazine isethionate.

4. A method according to claim 1 wherein the anxiety disorder is generalized anxiety disorder.

5. A method according to claim 1 wherein the anxiety disorder is simple phobia or panic disorder.

6. A method according to claim 1 wherein the anxiety is associated with obsessive compulsive disorder or with post-traumatic, stress disorder.

7. A method according to claim 1 wherein the anxiety disorder is associated with schizophrenia, a mood disorder or a major depressive disorder.

8. A method according to claim 1 (wherein the anxiety disorder is associated with an organic condition.

9. A method according to claim 8 wherein the organic condition is Parkinson's disease or multiple sclerosis.

* * * * *